(12) United States Patent
Coppi

(10) Patent No.: US 7,226,476 B2
(45) Date of Patent: Jun. 5, 2007

(54) PROSTHESIS FOR LARGE BLOOD VESSELS

(75) Inventor: Gioacchino Coppi, Modena (IT)

(73) Assignee: G.A.M.A.-H.S. S.r.L., Bologna (IT)

( * ) Notice: Subject to any disclaimer, the term of this patent is extended or adjusted under 35 U.S.C. 154(b) by 94 days.

(21) Appl. No.: 10/507,517

(22) PCT Filed: Nov. 24, 2003

(86) PCT No.: PCT/IT03/00767

§ 371 (c)(1),
(2), (4) Date: Sep. 14, 2004

(87) PCT Pub. No.: WO2004/052240

PCT Pub. Date: Jun. 24, 2004

(65) Prior Publication Data

US 2005/0119729 A1    Jun. 2, 2005

(30) Foreign Application Priority Data

Dec. 6, 2002   (IT) .............................. MO02A0349

(51) Int. Cl.
  *A61F 2/06* (2006.01)
(52) U.S. Cl. .................... 623/1.27; 623/1.35; 623/3.26
(58) Field of Classification Search ................. 623/1.1, 623/1.11, 1.13, 1.14, 1.27, 1.32, 1.35, 1.36, 623/3.1, 3.26; 606/153, 198, 191–195
See application file for complete search history.

(56) References Cited

U.S. PATENT DOCUMENTS

| | | | | |
|---|---|---|---|---|
| 5,800,514 A | * | 9/1998 | Nunez et al. | 623/1.51 |
| 5,906,641 A | * | 5/1999 | Thompson et al. | 623/1.15 |
| 5,989,207 A | * | 11/1999 | Hughes | 604/8 |
| 6,110,201 A | * | 8/2000 | Quijano et al. | 623/2.1 |
| 6,398,807 B1 | | 6/2002 | Haverkost et al. | |
| 6,409,757 B1 | | 6/2002 | Tanner et al. | |
| 6,814,752 B1 | * | 11/2004 | Chuter | 623/1.35 |
| 7,022,134 B1 | * | 4/2006 | Quijano et al. | 623/1.24 |
| 2002/0058992 A1 | * | 5/2002 | Greenhalgh | 623/1.35 |

FOREIGN PATENT DOCUMENTS

| | | |
|---|---|---|
| AU | 729 443 | 2/2001 |
| WO | WO 02 35988 | 5/2002 |

* cited by examiner

Primary Examiner—David J. Isabella
(74) Attorney, Agent, or Firm—Young & Thompson

(57) ABSTRACT

A prosthesis for large blood vessels includes a main conduit. At least one tract of the main conduit is subdivided into a plurality of smaller conduits located parallel to one another.

6 Claims, 2 Drawing Sheets

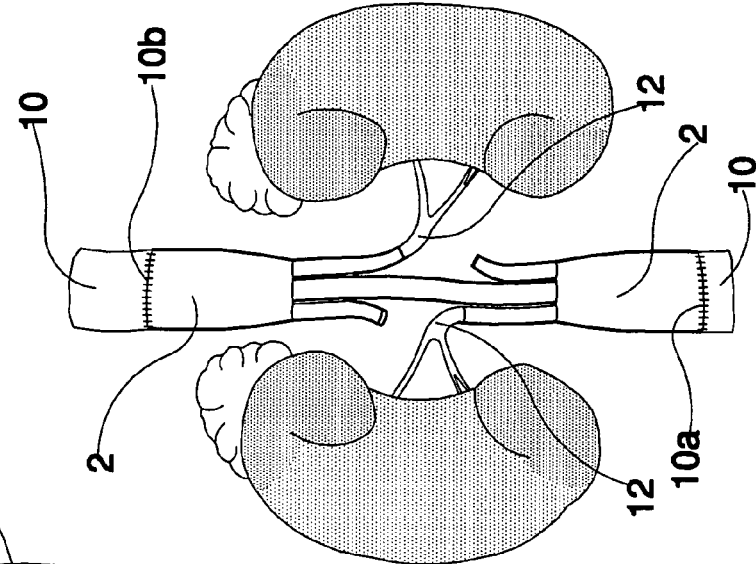
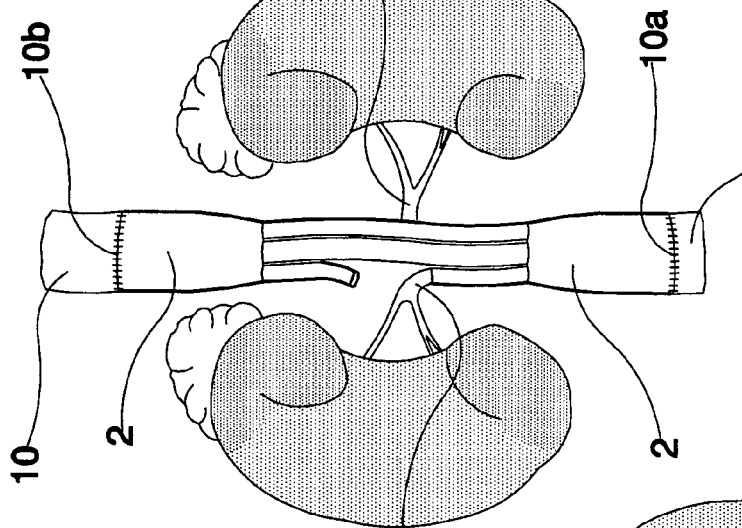
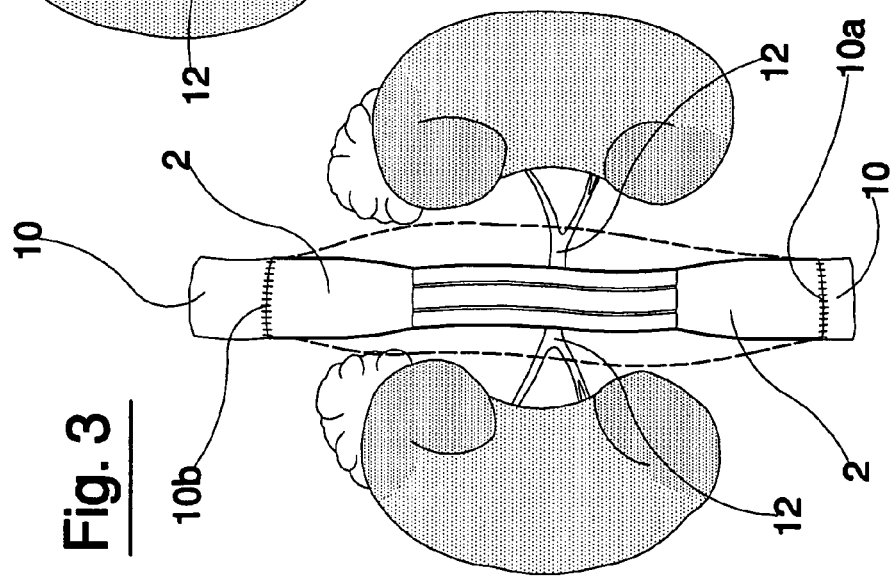

PROSTHESIS FOR LARGE BLOOD VESSELS

TECHNICAL FIELD

The invention relates to the field of prostheses used in treatment of thoracic-abdominal aneurysm.

BACKGROUND ART

The thoracic-abdominal aneurysm is largely a progressive yielding, fatal upon breaking, of the walls of the thoracic and abdominal aorta. As there is no possible medical therapy available, the pathology can only be treated by surgical intervention, which involves a large-scale thoracic laparotomy and substitution of the dilated tract with a straight tubular prosthesis. The visceral blood vessels and sometimes the intercostal arteries are connected to the prosthesis.

The surgical operation is carried out usually according to two main techniques, often used in combination.

The first of these techniques, also known as the De Bakey method, involves clamping (hemostasis) of the tract of aorta downstream of the aneurysm, a first sectioning of the aorta itself and the suturing of the prosthesis to the first section, and the clamping of the tract of aorta upstream of the aneurysm, a second sectioning of the aorta and the suturing (anastomosis) of the prosthesis to the second section. Then the visceral branches are sutured to the prosthesis with or without interpositioning of prosthetic segments. This technique exposes the patient to quite long operations with relevant haemorrhaging, but guarantees good blood circulation downstream of the aneurysm.

The second technique, also known as the Crawford method, is based on the speed of performance of the operation. The aorta is clamped upstream and downstream of the aneurysm. The aorta is sectioned upstream and downstream of the aneurysm, hemostasis is performed on any arteries connected to the sectioned tract of aorta, and the prosthesis is applied with rapid suturing to the two sections.

The visceral and intercostal arteries from the sectioned tract of aorta are then sutured to the prosthesis, preferably without interpositioning of prosthetic segments in order not excessively to extend operation time. The technique implies that during the operation the circulation downstream of the thorax is practically stopped. If possible, in anastomosis of the visceral and intercostal arteries, patches of aortic sections surrounding the original connection points of the arteries are re-used.

Although the results obtained using the techniques are satisfactory in a majority of the cases, with the patients' progressing to full recovery, there are however not inconsiderable risks connected to the importance of the surgical operation itself. The rate of mortality during or immediately following surgery, together with post-operational respiratory difficulties and kidney failure, can reach up to 20%. There is also a risk of about 20% of paraplegia, leading many patients to refuse to undertake the operation.

Paraplegia, as well as the other complications, is essentially due to a blockage in arterial circulation to the lower parts of the body. This blockage, which is of a length correlated to the difficulty of performance of the operation, can obviously lead to medullar ischemia and therefore to paralysis of the lower limbs.

To limit the risk of paraplegia temporary aortic by-passes are used, with extracorporeal circulation tubing taking blood from upstream of the aneurysm and sending it to the lumbar and hypogastric arteries. The inflow of blood to these arteries guarantees a sufficient vascularization of the medulla and the abdominal organs, very considerably reducing risks of ischemia. The use of extracorporeal circulation, however, involves considerable use of anticoagulants, especially if a pump is used, as is sometimes the case; in all cases, however, long operation times are needed.

SUMMARY OF THE INVENTION

The main aim of the present invention is to provide a prosthesis for large blood vessels which limits operation times for treatment of thoracic-abdominal aneurysm, thus also reducing duration of hemostasis in the aorta.

A further aim of the present invention is to maintain the blood circulation downstream of the aneurysm during the anastomosis operation on the various blood vessels branching off from the affected tract.

BRIEF DESCRIPTION OF THE DRAWINGS

Further characteristics and advantages of the present invention will better emerge from the detailed description that follows of a prosthesis for large blood vessels, in a preferred but non-exclusive embodiment of the invention, illustrated purely by way of a non-limiting example in the accompanying figures of the drawing, in which:

FIG. 3 is a second example of use of the prosthesis of FIG. 1;

FIG. 4 is a third example of use of the prosthesis of FIG. 1;

FIG. 5 is a fourth example of use of the prosthesis of FIG. 1.

DETAILED DESCRIPTION OF THE PREFERRED EMBODIMENTS

Figure 1:
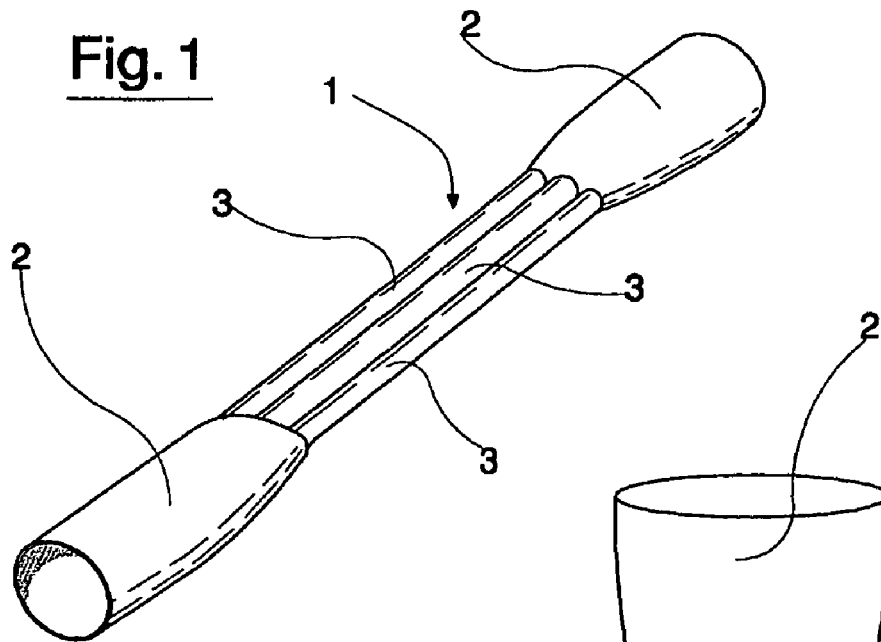
FIG. 1 is a perspective view of a prosthesis according to the present invention.

With reference to the figures of the drawings, 1 denotes in its entirety a prosthesis according to the present invention. It comprises a main conduit 2, at least a tract of which is subdivided into a plurality of small conduits 3 located parallel to one another.

The small conduits 3 each exhibit an internal calibre which is smaller than the main conduit 2 and the overall section of the small conduits 3 is about the same as that of the main conduit 2. The flow of blood entering the main conduit 2 is sub-divided into the small conduits 3.

The small conduits 3 are also independent of one another. They exhibit lateral walls which are distinct one from another, so that they can be manipulated and used separately. The small conduits 3 are for example three in number, one of which may exhibit a larger calibre than the remaining two thereof.

The main conduit 2 and the small conduits 3 are made of a bio-compatible material which has only a small elastic deformability in a transversal direction and a considerable elastic deformability in a longitudinal direction.

The application of the prosthesis of the present invention can be made in the following stages.

After having approximated the length of prosthesis required, distal clamping is performed and distal anastomosis 10a to the aorta 10 is carried out. Subsequently proximal clamping is performed and the aneurysm opened with clamping of the branching vessels in the tract affected by aneurysm. Proximal anastomosis 10b is then performed.

Figure 2:
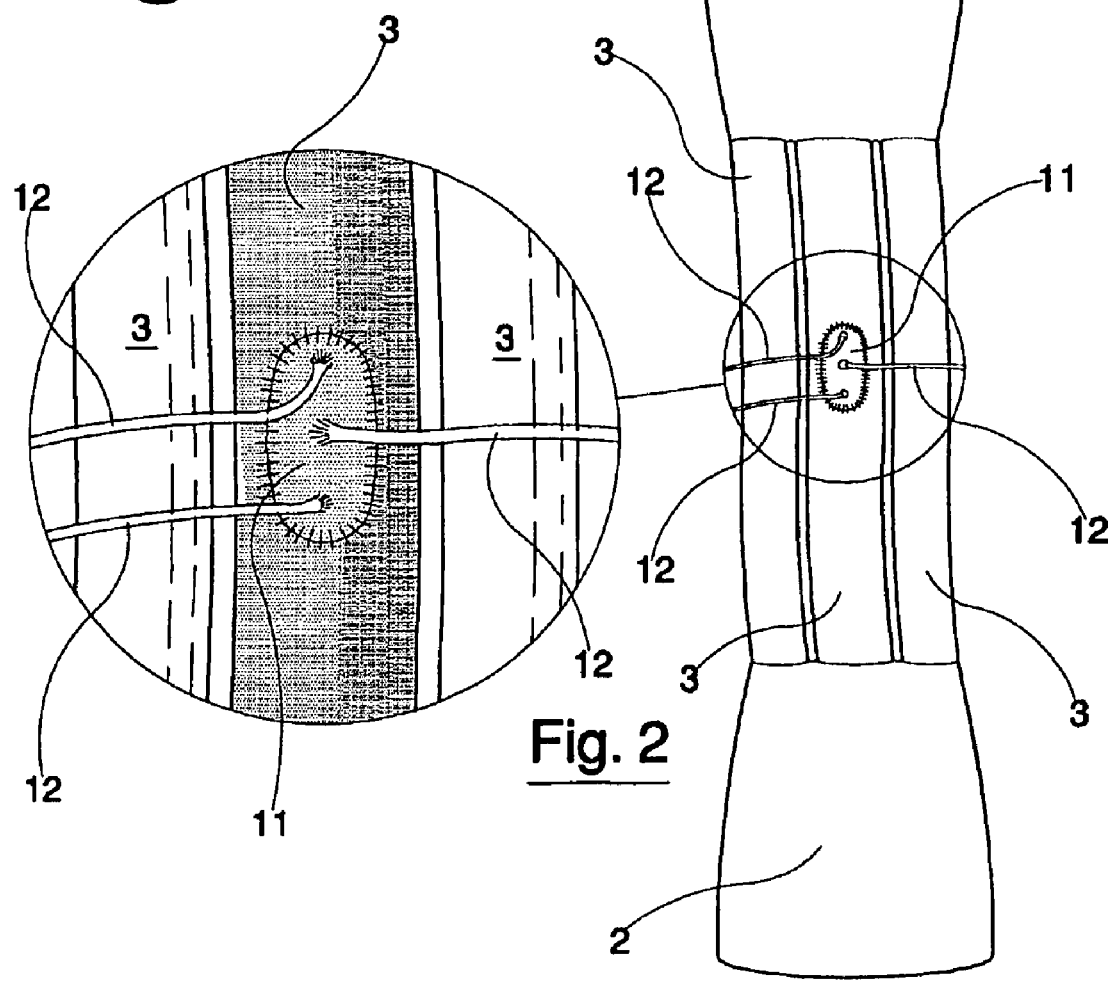
FIG. 2 is a first example of use of the prosthesis of FIG. 1.

Once the two suturing operations have been carried out, the clamps can be removed and abdominal and medullar blood circulation restored. In this calm situation the anastomosis of the branch vessels 12 from the tract subject to aneurysm can be carried out; the branch vessels 12 are sutured to the prosthesis while blood circulation is maintained through the other small conduits 3. As can be seen in FIG. 2, the branch vessels 12 can be sutured with the use of small patches 11 of original aortic matter surrounding the ends of the vessels and cut away with the vessels themselves. These can be sutured onto the largest of the small calibre conduits 3. If this technique is not possible, the small calibre conduits 3 can be used for end-to-end anastomosis between the prosthesis and the branch vessels 12 originating from the tract affected by aneurysm, while circulation is maintained through the small conduit 3 of largest calibre (FIGS. 3, 4, 5). Alternatively a small conduit 3 can be used to create a temporary by-pass of the prosthesis itself.

The application of the prosthesis of the present invention guarantees a high degree of liberty of action to perform the required anastomosis, whether pre-determined or decided during the course of the actual operation.

The duration of the hemostasis is thus limited to the time required for carrying out the proximal and distal anastomosis of the prosthesis to the aorta, reducing by a very considerable degree the risk of medullar or abdominal ischemia.

The invention claimed is:

1. A prosthesis for large blood vessels, comprising:
a main conduit having first and second ends, at least one intermediate tract of said main conduit is subdivided between said first and second ends into at least three smaller conduits located parallel one to another, that rejoin with said main conduit after being subdivided.

2. The prosthesis of claim 1, wherein the smaller conduits each have an internal calibre which is smaller than an internal calibre of the main conduit.

3. The prosthesis of claim 2, wherein an overall section which is a sum of sections of the smaller conduits is approximately equal to a section of the main conduit.

4. The prosthesis of claim 3, wherein the smaller conduits are independent one from another.

5. The prosthesis of claim 1, wherein one of the smaller conduits exhibits a greater calibre than two of the smaller conduits.

6. The prosthesis of claim 5, wherein the main conduit and the smaller conduits are made of a bio-compatible material which exhibits a smaller elastic deformability in a transversal direction thereof and a greater elastic deformability in a longitudinal direction thereof.

* * * * *